United States Patent [19]

Dommergues et al.

[11] 4,155,737

[45] May 22, 1979

[54] MICROBIOLOGICAL PROCESS FOR CONTROLLING THE PRODUCTIVITY OF CULTIVATED PLANTS

[75] Inventors: Yvon R. Dommergues; Gia D. Hoang, both of Dakar, Senegal; Charles Diviés, Dijon, France

[73] Assignee: Agence Nationale de Valorisation de la Recherche (ANVAR), Neuilly sur Seine, France

[21] Appl. No.: 891,920

[22] Filed: Mar. 30, 1978

[30] Foreign Application Priority Data

Apr. 5, 1977 [FR] France .................................. 77 10254

[51] Int. Cl.² ............................................. C05F 11/08
[52] U.S. Cl. .................................... 71/7; 71/6; 71/27; 47/DIG. 10; 195/4
[58] Field of Search ............... 47/D9, D10, 58; 195/54, 195/59, D11, 68, 65; 71/27, 6, 7, 79

[56] References Cited

U.S. PATENT DOCUMENTS

| 334,343 | 10/1920 | Diller | 195/59 |
|---|---|---|---|
| 2,098,918 | 5/1934 | Hendrickson | 195/54 |
| 3,205,060 | 9/1965 | Lindert | 71/1 |
| 3,933,458 | 1/1976 | Philipp | 71/11 |

*Primary Examiner*—Joseph Scovronek
*Assistant Examiner*—Chris Konkol
*Attorney, Agent, or Firm*—Alan H. Levine

[57] ABSTRACT

According to the invention, the productivity of cultivated plants is controlled by a microbiological process. At least one telluric microorganism having a favorable rhizospheric effect on a plant is embedded in a polymer gel. Fragments of the gel are then inoculated into the rhizosphere of the plant. The invention also relates to a process for preparing the required fragments of polymer gel. Polymerization of the gel is carried out in the presence of a culture of the desired microorganism, and the polymer block is thereafter broken up prior to use.

19 Claims, No Drawings

MICROBIOLOGICAL PROCESS FOR CONTROLLING THE PRODUCTIVITY OF CULTIVATED PLANTS

The present invention relates to a process intended for controlling the productivity of cultivated plants.

It has been known for a long time that there is between higher plants and the microorganisms in the soil a number of very complex interactions which act directly or indirectly on the productivity of plants.

Among the best known of these interactions, we should firstly mention the cmpulsory symbiosis existing between the bacteria of the Rhizobium species and the leguminous plants. These bacteria, which are present in the nodules of the leguminous plants, allow the leguminous plants, unlike other plants, to use the molecular nitrogen in the atmosphere as source of nitrogen.

There are a large number of other interactions between microorganisms arising from the soil and plants, but these are symbiotic partnerships which fix nitrogen in the case of the leguminous plants which have been examined more fully.

About 50 years ago, research into these symbioses led to the development of commercial preparations containing Rhizobia intended to "bacteriolyse" the seeds of leguminous plants or to be inoculated into the soil and thus to increase the nitrogen yield of the leguminous plants.

These commercial preparations are presented either in the form of a liquid bacterial suspension or in the form of a bacterial suspension adsorbed on solid supports such as peat, diatomite etc.

This type of preparation has two great disadvantages which, up until now, could not be overcome or even diminished:

(1) The survival rate of inoculated microorganisms is very low owing to the intervention of processes of antagonism such as competition, predation, antibiosis, or physico-chemical factors such as acidity, excessive temperature, dessiccation;

(2) Contact between inoculated microorganisms and the plant's root system is very uncertain;

(3) Conservation and manipulation of this species of inoculum are awkward and the conservation periods are generally quite limited.

In fact, it should be taken into consideration that the introduction into a non-sterile soil of foreign microorganisms causes a reaction of the microflora and microfauna of this soil which will tend to eliminate the "intruders" which, in the majority of cases, will not be able to survive or will become the prey of the autochthonal organisms. In addition, it is quite rare for the inoculated microorganism to find all of the physical and chemical conditions in the soil which will allow it to develop and even sometimes to survive.

Finally, with this type of preparation, the microorganisms, once they have been inoculated into the soil and if they survive, tend to disperse in the soil and do not remain in contact with the roots of the plant, hence wide variations in the results observed in the plants.

The applicant has discovered a process for overcoming the disadvantages listed above.

The invention relates to a microbiological process intended to control the productivity of cultivated plants, characterised in that fragments of polyme gel containing at least one telluric microorganism having a favourable Rhizospheric effect which tolerates inclusion in the said gel are inoculated into the rhizosphere of the said plants.

The term "rhizosphere" as used in the present text, designates all of the regions of the soil in contact with the roots of the plant which constitute the rhizosphere in the strict sense of the word as well as the very surface of the roots which is frequently known as rhizoplane.

The term "telluric microorganism" is interpreted as microorganisms capable of living in the soil, whether aerobic, anaerobic or microaerophile. They may be wild microorganisms or acclimatised microorganisms and bacteria or yeasts, fungi and related microorganisms.

By the term "telluric microorganism having a favourable rhizospheric action" we mean microorganisms capable of living in the soil, either in compulsory symbiosis with a root system or in association without compulsory symbiosis but in the rhizosphere of at least one cultivated plant, and which have a favourable rhizospheric action.

By "favourable rhizospheric effects" we firstly mean an action which modifies the rhizosphere from the energy, physical, chemical and/or biological points of view in a way which is favourable to the cultivated plant. This favourable rhizospheric effect will essentially be an improvement in the assimilation of nutritive substances in the atmosphere or in the soil, particularly nitrogen, phosphorus and potassium. Other types of desirable rhizospheric effects are also considered, in particular:

acceleration or, on the other hand, inhibition of the growth of the plants by the production of chemical substances such as auxinic substances, protection against pathogenic microorganisms by the production of antibiotic substances or predation of these microorganisms, symbiosis of mycorhizian type.

The term "microorganism tolerating inclusion (or embedding in the said gel" means microorganisms which are able to tolerate the conditions of inclusion in this gel, that is to say, in general, the polymerisation conditions and the reagents of polymerisation and are capable of multiplying from the gel, providing, of course, that they find a desirable environment.

This process allows the contact between the root system and the microorganisms having desirable rhizospheric action to be improved and also allows the said microorganisms to be protected from antagonistic actions.

The process according to the present invention is carried out more particularly with bacteria, in particular diazotrophic bacteria, or microorganisms which solubilise the insoluble phosphates and/or which solubilise the potassium in silicates containing potassium.

From among the diazotrophic bacteria, we should mention more particularly the bacteria having compulsory symbiosis with the host plant such as the Rhizobia and the bacteria having non-compulsory symbiosis with the host plant, such as the SARFA (rhizospheric associating symbiosis which fixes nitrogen) bacteria, such as the Spirilla or Enterobacter.

The microorganisms which solubilise the insoluble phosphates are selected particularly from the telluric bacteria of the Bacillus, Pseudomonas, Enterobacter and micromycete species.

The process according to the present invention is more particularly intended to improve the nitrogen yields of the leguminous plants and is more particularly applicable to the cultivation of soya using Rhizobium but also allows an improvement in the nitrogen yields of cereals such as rice, by utilising the SARFA microorganisms such as Spirillum, while at the same time reducing the consumption of conventional chemical fertilisers.

Inoculation is preferably performed at a depth of the order of 5 to 15 cm in the soil, depending upon the strain and the nature of the soil.

Thus, the enclosed strain will have to be inoculated nearer to the surface of the soil, if this strain requires oxygen and inoculation will have to be fairly close to the surface in soils of defective structure (beating structure) where diffusion of the oxygen is insufficient.

The quantity of inoculum required can vary within a very wide range depending upon the strain and the plant treated particularly, for example, for soya, the Rhizobium may be brought to concentrations of between $10^7$ and $10^9$ bacteria/plant.

Inoculation may be performed by known processes either during sowing or afterwards, or even beforehand in certain cases. In particular, the fragments of gel may be mixed with the seeds to effect inoculation.

In a preferred embodiment, inoculation is carried out as follows:
 (a) The polymer gel which has been conserved in the cool state (moist) in a buffer solution or physiological water is crushed finely;
 (b) This crushed material is diluted with a certain quantity of soil to be inoculated, about 10 times the volume of crushed material, to form an inoculum;
 (c) The inoculum is applied in the vicinity of the seeds in the sowing furrow or round the seed holes, preferably by mixing it with the soil over a depth of 5 to 15 cm.

The dose of polymer gel to be applied varies from 0.5 to 2 ml per plant and depends upon the concentration of the gel in microorganisms of the plant to be treated and particular of the soil, thus in the case of soil having phenomena of competition, it is necessary to provide a maximum dose.

Of course, it is possible to combine several types of microorganisms when carrying out the process according to the present invention. This type of association may be produced either by providing several strains of microorganisms in the same gel, providing that these strains are compatible, that is to say do not act undesirably upon each other, or, preferably, by inoculating fragments of several gels containing different strains of microorganisms.

In particular, in this embodiment of the process according to the invention, it is possible to use strains of microorganisms having different desirable rhizospheric effects, in particular strains which each act on the assimilation of a particular element, nitrogen, phosphorus and potassium.

But we also take into consideration the use of strains which differ in their sensitivity to oxygen, that is to say that the strains used may be aerobic, anaerobic or microaerophile; in this case, we would propose that they be inoculated at different depths in the soil, aerobic strains being inoculated in the surface area, anaerobic strains fairly far from the surface and microaerophile strains at an intermediate level.

The gels which may be used in the process according to the invention are preferably porous, 3-dimensional, slightly cross-linked synthetic polymers, as will be described in more detail below, or mineral gels such as silica gels.

The present invention also relates to a process for the preparation of gels which may be used for carrying out the process according to the invention as well as the gels obtained by this process.

This process for preparing gels is characterised in that:

A strain which can be embedded in the gel used is selected from among the strains having the desired favourable rhizospheric effect;

The gel is polymerised in a buffer medium containing the said strain in suspension;

The block obtained is washed with a buffer medium or a culture medium of the said strain;

The polymer block obtained is broken up;

The fragments obtained are stored in a buffer medium at low temperature;

The fragments of gel are reactivated prior to use by incubation in a culture medium of the said strain; or:

a strain which can be embedded in the gel used is selected from among the strains having the desired favourable rhizospheric effects;

the gel is polymerised in a microorganism culture;

the block obtained is washed in water;

it is stored in a buffer medium or in physiological water at a temperature of between 4° and 10° C.;

the block is crushed prior to use.

The stage of selection is performed by carrying out polymerisation in the presence of the said strain and by checking that the enclosed strain retains the ability to multiply after incubation of the gel obtained in a culture medium. Thus, for diazotrophic bacteria, three categories of bacteria were determined, using a polyacrylamide gel:

(1) Bacteria which can not be embedded in the polyacrylamide gel; for example, certain strains of Azotobacter. Once embedded, these bacteria lose the ability to multiply.

(2) Bacteria which can be embedded in the polyacrylamide gel but only find the ability to multiply after a very long reactivation period (several days to a week), Example: Certain strains of *Spirillum lipoferum*.

(3) Bacteria which can be embedded in the polyacrylamide gel and are able to multiply after a relatively short reactivation period (of the order of 1 to 3 days); Example: Rhizobium sp., *Enterobacter cloacae*, Beijerinckia sp.

These are the bacteria belonging to category 3 which are capable of giving the most attractive results for carrying out the process according to the present invention.

Polymerisation is carried out in known manner, preferably using a hydrophilic monomer such as acrylamide in the presence of a cross-linking agent such as N,N'-methylene-bis-acrylamide in the presence of a polymerisation catalyst. Polymerisation is carried out in a buffer medium containing the strain of microorganism in suspension. The polymerisation conditions are determined, in particular the quantity of cross-linking agent, so as to obtain a porous 3-dimensional structure.

Other polymers of this type which may be used when carrying out the present invention are described in French Pat. Nos. 75,24509 and 2,171,108.

In addition, the polymerisation conditions are selected so as to limit the reaction time as much as possible and the polymer obtained is washed so that the microorganisms are in contact for the minimum time with the catalyst and the by-products of the reaction.

If the polymer gel is of the colloid type, for example mineral, the process is carried out in the same way as above, either by preparing the colloid in the buffer medium containing the strain of microorganism or by preparing the colloid in dispersed form aside and making it "set" in the buffer medium.

The block of gel obtained after polymerisation may be broken up by any known means, in particular by cutting. Although the size and the shape of the fragments obtained do not seem to have a significant influence when carrying out the process according to the present invention, small cubes of about one-eighth of a cubic centimeter have given good results.

As it is necessary in the agricultural field to have available at the moment of sowing a sufficient quantity of inoculum which must therefore be prepared and stored, fragments of gel obtained are stored at low temperature of the order of 2° to 10° C., preferably 5° to 6° C. in a buffer medium.

It has surprisingly been observed that the inoculum could be stored very well under these conditions, providing that the precaution has been taken prior to use of reactivating the said gel, although this is not always necessary. The reactivated gels contain in addition to the embedded microorganisms the same microorganisms adsorbed on their surface. This reactivation is carried out by inoculating the fragments of gel into a culture medium at a temperature preferably between 27° and 30° C. with light stirring for a period of about 3 to 7 days depending upon the strains embedded.

The present invention also relates, as a means for carrying out the process according to the present invention, to the fragments of gel obtained by the said process.

The cubes of gel obtained may be used as they are or may be coated in various products which are used in plant chemistry such as tricalcium phosphate, industrial or agricultural waste.

The examples below illustrate certain characteristics of the invention but without limiting it.

EXAMPLE 1

Process for preparing the gel

A bacterial suspension of 5 to 10 ml of bacteria deposit suspended in 150 ml of phosphate buffer having the following composition is introduced into a serum bottle

| $PO_4KH_2$ | : | 2 g |
|---|---|---|
| $PO_4Na_2H$ | : | 2 g |
| Water | : | 1000 ml |

23.75 g of acrylamide are dissolved in 50 ml of phosphate buffer (solution A) and 1.25 g of N,N'-methylene-bis-acrylamide are dissolved in 50 ml of phosphate buffer (solution B). THese solutions A and B above are added one after the other to the bacterial suspension with stirring. 0.250 g of ammonium sulphate are dissolved in about 3 ml of phosphate buffer, this solution is added to the above preparation with continued stirring.

The mixture obtained is introduced into the production mold with stirring using a sterile glass rod, 150 μl of N,N,N',N'-tetramethylethylene-diamine are then added and stirring is continued until the gel sets. The setting of the gel is accelerated if care has been taken to keep the acrylamide and the bis-acrylamide away from moisture in a dessiccator. The gel is removed from the mold once it is sufficiently cool, this taking a maximum of ten minutes. This gel is washed immediately either in a phosphate buffer solution or in a culture medium, half diluted. The gel is then broken up into blocks of variable sizes, cubes with half centrimeter edges having given excellent results.

The gels thus obtained are stored in buffer solutions kept at a temperature of between 4° and 6° C.

EXAMPLE 2

SARFA symbiotic association

The microorganisms used in this example are *Spirillum lipoferum*. Gels containing microorganisms were prepared by using process in the previous example. After fragmentation, the small blocks obtained are reactivated by incubation at 27° to 30° C. in a culture medium for about seven days with light stirring.

| Culture medium for *Spirillum lipoferum* | |
|---|---|
| $KH_2PO_4$ | : 0.400 g |
| $K_2HPO_4$ | : 0.100 g |
| $MgSO_4 7H_2O$ | : 0.200 g |
| NaCl | : 0.100 g |
| $CaCl_2$ | : 0.020 g |
| $FeCl_3$ | : 0.010 g |
| $NaMoO_4 2H_2O$ | : 0.002 g |
| $NH_4Cl$ | : 0.013 g |
| Yeast Extract | : 0.100 g |
| Malic acid | : 3.2 g (neutralised to pH 7 with KOH) |

Small blocks of polyacrylamide gel (one-eighth of $cm^3$) containing *Spirillum lipoferum* are inoculated into the soil to a depth of between 10 and 15 cm in the vicinity of the root system of rice because in this case microaerophilic strains which are facultative anaerobes are being used.

Once the root system has largely penetrated the small cubes of gel, the entire system is sampled and observed under an ultracryomicroscope. The following results are observed:

(1) the cubes of gel have an attracting effect on the roots,
(2) the roots penetrate the cubes of gel very easily without making them break up,
(3) there is hardly any solution of continuity between the root cortex and the gel,
(4) The main roots are able to give off secondary roots within the cubes of gel which act as inoculum reservoirs.

The inoculation process carried out in this way allows perfect contact to be established between the permanent source of inoculum constituted by the polyacrylamide gel and the root.

EXAMPLE 3

Inoculation of soya

In this example, the effect of inoculation by the conventional process is compared to the effect of inoculation according to three variations of the process according to the present invention, in order to examine the influence of the process according to the present invention on nitrogen fixation and the yield of soya cultivated in a vegetation vessel.

For this examination, a Jupiter variety of soya was used in a Dior soil.

The microorganisms having a favourable rhizospheric effect used are Rhizobium japonicum in the form of two mutants, the G3S mutant resisting streptomycine (1000 µg per ml of culture medium), the G2Sp mutant resisting spectinomycine (500 µg per ml of culture medium). These two mutant strains of Rhizobium are available from the INRA collection in Dijon, 7 rue Sully, 21000 Dijon.

The vegetation vessels having a capacity of 5 liters contain 6.7 kg of Dior soil, the bottoms of the vessels are covered with a layer of 200 g of quartz gravel, combined nitrogen is not added, phosphorus and potassium are added in the following form:

phosphorus is added in the form of phosphate (40% of $P_2O_5$) in solution in two additions to a dose of 0.478 g per vessel;

potassium is added in the form of KCl (60% of $K_2O$) in a dose of 0.319 g per vessel.

(These doses correspond to additions of 50 kg of $P_2O_5$ per hectare and of 50 kg of $K_2O$ per hectare).

Three soya seeds are sown in each vegetation vessel and, one month after sowing, the plants are thinned to leave only one plant per vessel.

The following tests are carried out:
(1) a control sample: no inoculation,
(2) conventional inoculation with a liquid culture of Rhizobium,
(3) inoculation according to the present invention, the cubes of polyacrylamide gel being placed at a depth of 5 cm,
(4) the same treatment as in (3) but with the cubes of gel being coated with tricalcium phosphate,
(5) same treatment as in (3) but the cubes of polyacrylamide gel are placed at a depth of 15 cm.

The inoculums were prepared in the following manner:

The polyacrylamide gels are prepared according to the method described in Example 1, they are then stored at 5° to 10° C. for one month in a phosphate buffer solution having the following composition:

| | | |
|---|---|---|
| $KH_2PO_4$ | : | 2 g |
| $Na_2HPO_4$ | : | 2 g |
| Streptomycine (for the G3S strain) | : | 200 g |
| Spectinomycine (for the G2Sp strain) | : | |
| water | : | 1000 g |

Before inoculating the soil, the polyacrylamide gels containing embedded bacteria have been cut into cubes of one-eighth of a cubic cm. and reactivated by incubation on an agitation table in the conventional culture medium for Rhizobium.

| Culture medium | | |
|---|---|---|
| $K_2HPO_4$ | : | 0.5 g |
| $MgSO_4\ 7H_2O$ | : | 0.2 g |
| NaCl | : | 0.2 g |
| $CaCO_3$ | : | 0.1 g |
| Mannitol | : | 10 g |
| yeast water | : | 100 ml |
| distilled or permuted water | : | 900 ml |

Regulate to pH 7. Sterilise for 20 minutes at 120° C.

24 ml of gel cubes of ⅛ cm³ (that is about 200 cubes) are added per vegetation vessel, either at a depth of 5 cm or at a depth of 15 cm. The number of bacteria added per vegetation vessel is of the order of $7.10^8$ for the G2Sp strain and $0.7.10^8$ for the G3S strain.

During reactivation, the Rhizobium proliferated in the culture medium and these free bacteria were used as liquid inoculum. Conventional inoculation was carried out by addition to the top of the seed bed of 1 cm³ of the solution concentrated by centrifugation so as to add the same number of bacteria by this conventional process as in inoculation according to the process of the present invention.

Table I

| | Number of live bacteria added per vegetation vessel | |
|---|---|---|
| | Liquid Inoculum | Inoculum per bacteria embedded in polyacrylamide gel |
| G2Sp strain | $7 \cdot 10^8$ | $7 \cdot 10^8$ |
| G3S strain | $1 \cdot 0\ 10^8$ | $0.7 \cdot 10^8$ |

Each experiment was repeated five times.

When the plants had reached the stage of pod formation (60th day) the following analyses were carried out:

The nodules were counted and weighed and the nature of the strain responsible for nodulation was monitored on a medium which is selective toward streptomycine or spectinomycine, depending upon the strain used.

The fixing activity of the nitrogen is evaluated by the acetylene reduction method, the vegetation vase with the plant being placed in the chamber in which the acetylene was injected.

Evaluation of the yield of dry material from the aerial parts and the roots of the plant (by oven drying at 60° C.).

Evaluation of the nitrogen yield of the plant (Kjeldahl dosage).

The results are also analysed statistically, based on the test of the smallest significant difference.

The results obtained are classified in table II.

Table II

| | Nodules | | $N_2$ Fixing activity (nmole $C_2H_4$/h) | | Total Yield (g/plant) | | Yield of Aerial parts (g/plant) | |
|---|---|---|---|---|---|---|---|---|
| Tests | Number/Plant | Cool weight (g/plant) | Per Plant | Specific | Dry weight | Nitrogen | Dry weight | Nitrogen |
| 1 | $0^a$ | $0^a$ | 1000 | — | $4.43^a$ | $3.01^a$ | $2.15^a$ | $1.46^a$ |
| 2 | $4^a$ | $0.120^a$ | 26435 | 220 300 | $4.53^a$ | $3.79^a$ | $1.88^a$ | $2.69^a$ |
| 3 | $54^b$ | $1.434^b$ | 43710 | 33 300 | $7.43^b$ | $14.08^b$ | $5.35^b$ | $11.57^b$ |
| 4 | $72^c$ | $1.876^c$ | 49648 | 26 500 | $7.68^b$ | $14.11^b$ | $6.05^b$ | $11.39^b$ |
| 5 | $19^d$ | $1.252^b$ | 41575 | 33 200 | $4.63^a$ | $7.00^a$ | $3.19^c$ | $5.27^a$ |

In each of the columns, the results which do not differ significantly (P = 0.01) are labelled with the same letter. When the fixing activity of $N_2$ was determined by the acetylene reduction method, the number of repetitions made was insufficient to allow statistical interpretations of them.

Monitoring of the nature of the strain responsible for nodulation has revealed that practically all the nodules had been induced by infection with the G2Sp strain (resistance to spectinomycine). Under these conditions, it may be admitted that the results obtained would really have been the same if the inoculum had been added only in the form of Rhizobium G2Sp embedded in the dose of 200 cubes of one-eighth of cm$^3$ per plant.

EXAMPLE 4

Process for the preparation of the polymer gel 150 ml of a bacterial culture are introduced into a 300 ml beaker at the end of the exponential pahse (4 to 5 days in the case of *Rhizobium japonicum*). 50 ml of an acrylamide solution are added successively (solution A):

| acrylamide | 155 g |
|---|---|
| phosphate buffer (pH 7), qsp | 650 ml | and 50 ml of a solution of N,N'-methylene-bis-acrylamide (Solution B):

| N,N'-methylene-bis-acrylamide | 6.27 g |
|---|---|
| phosphate buffer (pH 7), qsp | 500 ml |

(The A and B solutions are filtered on high quality filter paper so as to obtain a clear solution, that is to say free from non-solubilised crystals), then 126 mg of ammonium persulphate (kept on dehydrating agent) dissolved in 3 ml of distilled water and finally 76 microliters of N,N,N',N'-tetramethyl-ethylene-diamine. The mixture is stirred with a glass rod for a few minutes; the gel sets in a mass at the end of 10 minutes. The gel is left to cool for a further 10 minutes and is removed from the mold. The gel is cut into slices having an approximately volume of 10 to 20 cm$^3$ and is washed immediately in a stream of tap water for a minimum of 24 hours. The gel thus obtained may be stored for a long time (up to one year) in a phosphate buffer solution or physiological water (NaCl: 8.5 g per liter) at a temperature of between 5° and 10° C.

The solution A cannot be treated in an autoclave; solution B can be treated in an autoclave. It results that if an aseptic product is desired (this not being necessary for use in situ), solution A must be sterilised by filtration. Phosphate Buffer:

| Phosphate Buffer: | |
|---|---|
| PO$_4$KH$_2$ | : 1 g |
| PO$_4$Na$_2$H | : 2 g |
| Distilled Water | : 1000 ml |
| The pH is 7.0 | |

EXAMPLE 5

The aim of this example is to determine the effect of crushing and drying the polymer gel on the infectivity of the inoculum towards soya and to determine the dose required for obtaining a result with is equivalent to that obtained by a liquid inoculum, taken as a reference.

The cv. Jupiter soya has been cultivated in a pot under shelter for five weeks in Dior soil containing phosphopotassium fertiliser (32 mg of P$_2$O$_5$+28 mg of K$_2$O per kg of soil).

The polymer gel prepared by the process in Example 4 as well as the liquid inoculum contained the same number of Rhizobium G2Sp, that is to say $5 \times 10^8$ per ml).

The results shown in Table III are the average of 5 repetitions. In columns 1 and 2, the figures labelled with the same letter do not differ significantly for P=0.05.

The fixation of N$_2$ (column 3) was determined by the method of the difference (difference between the total nitrogen content of the inoculated plants and the total nitrogen content of the non-inoculated control samples, therefore without Rhizobium). Since the dosages of nitrogen had been made on a sample of plant resulting from the mixture of the aerial parts of the plants subjected to the same treatment, it was not possible to carry out statistical analysis of the corresponding results (column 3).

It is observed that:
1. Crushing of the inoculum improves its infectivity considerably (for a same quantity applied).
2. The dose of application of the crushed inoculum is of the order of 2 ml per plant, in order to obtain a result which is comparable to that given by the liquid inoculum (prepared extemporaneously).
3. Dessication significantly reduces infectivity of the inoculum but it is interesting to note that, even when dried, the inoculum still retains relatively high infectivity if it is applied in a dose of 2 ml per plant.

Table III

Influence of the means of applying the inoculum in polymer gel on the fixaton of N$_2$ with soya. cv. Jupiter (strain of *Rhizobium japonicum* G2Sp)

|  | Cool weight of the nodules (mg/plant) (1) | Weight of the aerial parts (g/plant) (2) | N$_2$ fixed in the aerial parts (mg/plant) (3) |
|---|---|---|---|
| Non-inoculated control sample | 166 ab | 1239 a | 0 |
| Liquid inoculum (0.5 ml/plant) | 573 c | 2367 cde | 37.4 |
| Inoculum in polymer gel (0.5 ml/plant) | | | |
| cubed, dried | 85 a | 1499 ab | 3.0 |
| cubed, moist | 514 c | 1930 bed | 18.4 |
| crushed then dried | 109 a | 1424 ab | 0 |
| crushed, moist | 487 c | 1900 abcd | 24.5 |
| Inoculum in polymer gel (2 ml/plant) | | | |
| cubed, dried | 293 b | 1493 ab | 5.9 |
| cubed, moist | 489 c | 1721 abc | 20.1 |
| crushed, then dried | 537 c | 1872 abcd | 18.3 |
| crushed, moist | 561 c | 2407 de | 41.9 |

The values in a given column are not significantly different when the corresponding letters a, b, c, d, e, are the same.

EXAMPLE 6

The *Rhizobium japonicum* strain used is the G2Sp mutant which is resistant to spectinomycine (500 μg per ml of medium). This strain is available in the INRA collection in Dijon, 7 rue Sully, 21000 Dijon. We have checked, furthermore, that the effectiveness of this mutant was high since, in situ, in the absence of limiting factors, the fixation of $N_2$ is of the order of 300 to 400 kg/ha when this strain is inoculated in the soya cv. Jupiter.

The strain of Rhizobium G2Sp has been cultivated on the Wacek and Brill medium (1976, Crop Science, 16: 519–522)

|  |  |  |
|---|---|---|
| Mannitol | 10 | g |
| $K_2H\ PO_4$ | 0.5 | g |
| $Mg\ SO_4, 7H_2O$ | 0.2 | g |
| NaCl | 0.2 | g |
| $FeCl_3$ | 4.88 | mg |
| Difco yeast extract | 1 | g |
| Distilled water | 900 | ml | pH 7 was regulated with HCl N. Sterilisation was effected in the autoclave for 20 minutes at 120° C. Culture is effected on a stirring table for five days at 30° C. The soil used is a sandy soil (Dior).

The soya cv. Jupiter was sown in small plastic pots containing 50 g of soil. Plants of uniform size were selected for replanting when they had their first leaves (five days after sowing) in plastic vegetation vessels each containing 3 kg of soil.

The inoculum which had previously been diluted in soil was mixed with the soil in the top 10 cm of soil in the central region of the pot. Two types of inoculum were compared:

1. Inoculum in polymer gel prepared in accordance with the protocol described in Example 4 and applied in two doses (0.5 and 2.0 ml).
2. Conventional inoculum on peat
   high quality commercial inoculum
   inoculum on sterile peat prepared in the laboratory by sowing with the same culture as that used for embedding in polymer gel.

The same strain (G2Sp) was used in all the treatments, except for the "commercial inoculum" treatment (strain unknown).

The quantity of bacteria used was $5 \times 10^8$ per ml in the polymer gel and $5 \times 10^8$ bacteria in the peat prepared in the laboratory. Five repetitions were made for each treatment. The control sample was constituted by a polymer gel with embedded Rhizobium sterilised in an autoclave. The specific reducing activity of acetylene (ARA) was determined by the conventional method and expressed in micromoles of ethylene formed per g of dry nodule.

The nitrogen fixed in the aerial parts was determined by the method of difference, that is to say by subtracting the content of total nitrogen of the control plants (without nodules) from the content of total nitrogen in the plants with nodules for each of the different inocula. Analyses were carried out when the plants were 35 days old. Table IV shows (1) The inoculum in polymer gel allows fixation of $N_2$ which is double that resulting from the application of commercial inoculum although specific ARA and the weight of nodules are substantially the same.

(2) The increase in the dose of inoculum in polymer gel is translated by a substantial but not significant increase in the quantity of fixed nitrogen and this may be explained by an increase in the weight of nodules. Furthermore, the application of the high dose affords the advantage of clearly improving the reproducibility of the results.

(3) The inoculum in polymer gel gives results identical to inoculum on a peat base prepared in the laboratory, (sterile peat sown extemporaneously with the Rhizobium culture).

An accessory experiment has shown that the increase in the nitrogen content of the plant could not be attributed to use of the nitrogen entering the constitution of the actual polymer.

Table IV

| Comparison of the effect on the fixation of nitrogen by soya of two doses of inoculum in the polymer gel and two types of inoculum on a peat support. | | | | | |
|---|---|---|---|---|---|
|  | Number of nodules per plant | Dry weight of the nodules (g/plant) | Specific ARA (n mole $C_2H_4$ per h per g of dry nodule) | Dry weight of aerial parts (g/plant) | $N_2$ fixed in the aerial parts (mg/plant) |
| Inoculum in polymer gel | | | | | |
| normal (0.5 ml) | 74 a | 0.123 a | 107 a | 2.809 a | 30.2 a |
| normal (2.0 ml) | 89 a | 0.196 a | 128 a | 2.999 a | 44.5 a |
| Inoculum on peat | | | | | |
| commercial (0.5 g) | 124 a | 0.143 a | 104 a | 1.915 b | 14.2 b |
| prepared in the laboratory (0.5 g) | 116 a | 0.134 a | 133 a | 2.797 a | 31.3 a |
| Control sample | | | | | |
| Sterilised inoculum | 0 | 0 | 0 | 1.275 b | 0 |

The values in a given column are not significantly different when the corresponding letters a, b are the same.

EXAMPLE 7

NITROGEN-FIXING RHIZOSPHERIC ASSOCIATIVE SYMBIOSIS (SARFA)

The microorganism used in this Example is *Enterobacter cloacae* strain RO3, isolated from the rhizosphere of a rice. The gel is prepared in accordance with Example 4. The culture medium of *E. cloacae* is as follows:

|  |  |  |
|---|---|---|
| $KH_2\ PO_4$ | 500 | mg |
| $K_2H\ PO_4$ | 500 | mg |
| $MgSO_4$ | 200 | mg |
| NaCl | 100 | mg |
| $CaCl_2$ | 100 | mg |

-continued

| FeSO$_4$. 7H$_2$O | 10 mg |
| Solution of trace-elements | 1 ml |
| Glucose | 10 g |
| Difco potato extract | 1 g |
| Difco yeast extract | 100 mg |

The pH is regulated to 7.0 The solution of trace elements is prepared according to Augier (1956. Ann. Inst. Pasteur; 91, 759).

The inoculum in polymer gel is prepared in accordance with the protocol described above from a culture of 24 h of *E. cloacae*. The results of the corresponding experiment are shown in Table V.

The object of this experiment is to compare the liquid inoculum, the inoculum in silica gel and the inoculum in polymer gel, or in the case of sorghum, the stimulation of the fixation of rhizospheric nitrogen (free fixation of nitrogen) by *Enterobacter cloacae*.

Experimental apparatus

Seeds of sorghum cv. 51-69 were transplanted in a proportion of one per pot in pots containing about 800 g of sandy soil. Three types of inoculum ($4 \times 10^9$ bacteria per plant) were compared.

liquid inoculum (prepared extemporaneously)
inoculum in crushed silica gel
inoculum in crushed polymer gel
control sample (liquid inoculum treated in autoclave).

The inoculum was applied in the top 4-5 cm of the soil. Three repetitions were made for each treatment. When the plants were 33 days old, the fixation of N$_2$ was measured by the conventional method of acetylene reduction, incubation having been applied to the entire repotted plant plus soil system with the minimum of disturbance.

Results

The stimulation of rhizospheric fixation of N$_2$ by *Enterobacter cloacae* occurs only when the inoculum has been added in the form of polymer gel, the effect of this type of inoculum being highly significant.

EXAMPLE 8

Stimulation of rhizogenesis

The microorganism used in *E. cloacae* strain RO3 as in example 7; the conditions for the cultivation and preparation of the inocular are identical to those used in that example.

The object of this experiment is to compare the effectiveness of three types of inoculum (liquid inoculum, inoculum in silica gel, inoculum in polymer gel) with regard to the rhizogenic effect of the *Enterobacter cloacae* RO3 strain on sorghum cv. 51-69. The results are compiled in table VI.

Experimental apparatus

Seeds of sorghum cv. 51-69 were transplanted in a proportion of one per tube in PVC tubes of $25 \times 3$ cm containing 220 g of sandy soil and were placed in a phytotron at 28° C. with illumination of about 15000 lux and a photoperiod of 14 hours. Three repetitions were made per treatment.

The same types of inoculum were compared with those which had been used in example 7 except that the number of bacteria added per plant: $2 \times 10^9$ differs slightly. 20 days after commissioning the experiment, the weight of the aerial parts and the roots of the sorghum was determined.

Result

The rhizogenic effect of *E. cloacae* is only displayed in the case of inoculum in polymer gel, the stimulation of the rhizogenesis being highly significant.

Table V

| Comparison between three methods of inoculation with *Enterobacter cloacae* R03 on the fixation of N$_2$ (C$_2$H$_2$) in the rhizosphere of sorghum cv. 51-69 | |
|---|---|
| Reducing activity of acetylene (nmoles C$_2$H$_4$ per g of dry root per hour) | |
| liquid inoculum | 142 a |
| silica gel " | 222 a |
| polymer gel " | 1008 b |
| control sample (sterilised inoculum) | 187 a |

The values in a given column are not significantly different when the corresponding letters a, b are the same.

Table VI

Comparison between three methods of inoculation with *Enterobacter cloacae* R03 on the rhizogenesis of sorghum cv. 51-69

| | Dry weight in mg per plant | |
|---|---|---|
| | Roots | Leaves |
| liquid inoculum | 303 a | 331 a |
| silica gel inoculum | 268 a | 256 a |
| polymer gel inoculum | 846 b | 332 a |
| control sample (liquid inoculum treated in autoclave) | 276 a | 303 a |

The values in a given column are not significantly different when the corresponding letters a, b are the same.

EXAMPLE 9

Influence of embedding in polymer gel on the survival of *Rhizobium japonicum*

The same culture of *Rhizobium japonicum* G$_2$Sp was stored for 75 days at two different temperatures (4° C. and 30° C.) in three different forms:

liquid culture as it is
liquid culture on sterile peat support
culture embedded in polymer gel in cubes of about 1 ml, maintained in a phosphate buffer solution pH 7.

The rates of survival expressed by the percentage of the number of bacteria still living after storage in relation to the number of bacteria living prior to storage are indicated in table VII.

Counting was carried out by the conventional method of dilution and spreading over the Wacek and Brill medium (see example 6) in Petri boxes incubated at 30° C.

The results show that the embedding in polymer gel ensures very good survival even if the storage temperature is high (30° C.).

Table VII

Survival of *Rhizobium japonicum* stored for 75 days in a liquid medium on peat and embedded in polymer gel at two different temperatures (4° C. and 30° C.)

| | Survival rate (percent) | |
|---|---|---|
| Type of Storage | After 75 days of storage at 40° C. | After 75 days of storage at 30° C. |
| Liquid culture | 67 | <0.1 |
| Peat support | 62 | <0.2 |
| Polymer gel | 83 | 73 |

The above experiment shows that the process according to the present invention allows the number and particularly the weight of the nodules formed to be increased very significantly in relation to the conventional inoculation processes.

This property allows us to consider the introduction of new strains into a soil already having specific strains of Rhizobium. In other words, the use of the process according to the invention should allow the elimination of the handicap of competition which constitutes at present the major obstacle to the introduction in situ of the new strains obtained by geneticians.

According to the observations made, the root is not infected at the level of the root segment which passes through each cube of polyacrylamide gel but in a zone located immediately below the embedding. Embedding would act as an inoculum reservoir from which the bacteria would be liberated permanently and would multiply along the root and then infect the root as soon as they reach favourable sites of infection.

The nitrogen yield is improved very spectacularly by carrying out the process according to the present invention since the yield has practically quadrupled when the inoculum of embedded bacteria is placed at a depth of 5 cm. This increase is weaker in the case where the cubes of polyacrylamide gel are placed at 15 cm.

This unfavourable effect of positioning at depth is explained by the fact that in the experimental conditions adopted, the diffusion of the oxygen in depth is slight.

If the specific nitrogen fixing activity is considered, it is noted that it is about 10 times weaker in the case of inoculum by embedded bacteria. This is explained by the fact that the process according to the invention ends up over-equipping the plants with nodules and that a limiting factor intervenes which does not allow the complete expression of the nitrogen fixing activity by the system obtained, this limiting factor either being a vegetable factor (particularly photosynthesis) or a factor of the climatic environment for example insufficient luminous intensity at the moment of measurement or edaphic (for example phosphate dystrophia).

The process according to the present invention allows the intervention of the limiting factor to be eliminated with a high degree of certainty, this limiting factor often being caused by the inadequacey of efficient nodules provided in a leguminous plant.

We claim:

1. A microbiological process for controlling the productivity of cultivated plants, which comprises inoculating into the rhizosphere of a plant fragments of a polymer gel in which are embedded a least one telluric microorganism having a favourable rhizospheric effect and capable of being embedded in said gel.

2. A microbiological process according to claim 1, wherein the finely divided polymer gel is diluted with a predetermined quantity of the soil to be inoculated so as to obtain an inoculum, and this inoculum is applied in the vicinity of seeds of said plant by mixing it with the soil.

3. A microbiological process according to claim 2, wherein the finely divided polymer gel is obtained by cutting into fragments at least one block of polymer gel stored in a medium selected from the group consisting of buffer solutions and salt water.

4. A process according to claim 1, wherein the embedded microorganism is capable of multiplying from the polymer gel when the polymer gel is placed in a culture medium for said microorganism.

5. A process according to claim 1, wherein the polymer gel is selected from the group consisting of polyacrylamide gels and silica gels.

6. A process according to claim 5, wherein the polymer gel is a polyacrylamide gel.

7. A process according to claim 1, wherein the microorganism having a favourable rhizospheric affect is selected from the group consisting of diazotrophic bacteria, microorganisms solubilising insoluble phosphates, microorganisms solubilising potassium from potassium-containing silicates, microorganisms producing growth-regulating substances and microorganisms providing resistance to phytopathogenic agents.

8. A process according to claim 7, wherein the diazotrophic bacteria are selected from the Rhizobium species.

9. A process according to claim 7, wherein the diazotrophic bacteria used are selected from the group consisting of the Spirillum species and the Enterobacter species.

10. A process according to claim 7, wherein the microorganisms solubilising insoluble phosphates are selected from the group consisting of Bacillus, Pseudomonas, Enterobacter and Micromycete species.

11. A process according to claim 1, wherein the polymer gel is inoculated into the rhizosphere of the plants at a depth of between about 5 and 15 cm.

12. A process according to claim 1, wherein fragments of polymer gel containing a mixture of different species of microorganisms are inoculated.

13. A process according to claim 12, wherein the microorganisms used differ in their favourable rhizospheric effects.

14. A process according to claim 13, wherein the microorganisms used differ in their sensitivity to oxygen and are selected from the group consisting of aerobic, microaerophilic and anaerobic strains.

15. A process according to claim 1, wherein the polymer gel used is coated with a phosphate-containing product.

16. A process according to claim 1, wherein the plant is soya.

17. A process for preparing fragments of a polymer gel required for carrying out the process according to claim 1, comprising the following steps:
   (a) selecting a strain which can be embedded in the gel used from among the strains having the desired favourable rhizospheric effect;
   (b) polymerizing the gel in a buffer medium containing the said strain in suspension;
   (c) washing the block obtained in a medium selected from a buffer medium and a culture medium of the said strain;
   (d) breaking up the polymer block obtained;
   (e) storing the fragments obtained in a buffer medium at low temperature; and
   (f) reactivating the fragments of gel prior to use by incubation in a culture medium of the said strain.

18. A process for preparing fragments of a polymer gel required for carrying out the process according to claim 1, comprising the following steps:
   (a) selecting a strain which can be embedded in the gel used from among strains having the desired favourable rhizospheric effect;
   (b) polymerising the gel in a culture of the microorganisms;
   (c) washing the block obtained in water;
   (d) storing the washed block in medium selected from a buffer medium and salt water at a temperature of between 4° and 10° C.; and
   (e) cutting the block into fragments prior to use.

19. Fragments of reactivated gel obtained by the process in either of claims 17 or 18.

* * * * *